United States Patent
Kutzko et al.

(10) Patent No.: US 6,268,487 B1
(45) Date of Patent: Jul. 31, 2001

(54) PURIFICATION OF BIOLOGICALLY ACTIVE PEPTIDES FROM MILK

(75) Inventors: Joseph P. Kutzko, Southboro; Michael L. Hayes, Acton; Lee T. Sherman, Northboro, all of MA (US)

(73) Assignee: Genzyme Transgenics Corporation, Framingham, MA (US)

( * ) Notice: Subject to any disclaimer, the term of this patent is extended or adjusted under 35 U.S.C. 154(b) by 0 days.

(21) Appl. No.: 08/648,235

(22) Filed: May 13, 1996

(51) Int. Cl.[7] ................. C07K 1/14; C07K 1/16
(52) U.S. Cl. .......... 530/414; 530/412; 530/413; 530/416; 530/832; 435/69.1; 800/DIG. 1
(58) Field of Search ................. 530/414, 412, 530/413, 416, 832; 435/69.1; 800/DIG. 1

(56) References Cited

U.S. PATENT DOCUMENTS

| | | | |
|---|---|---|---|
| 4,485,040 | 11/1984 | Roger et al. | 260/122 |
| 4,644,056 | 2/1987 | Kothe et al. | 530/387 |
| 4,897,465 | 1/1990 | Cordle et al. | 530/387 |
| 5,175,013 | 12/1992 | Huang et al. | 426/565 |
| 5,178,894 | 1/1993 | Rudel | 426/549 |
| 5,256,294 | * 10/1993 | Van Reis | 210/637 |
| 5,256,437 | * 10/1993 | Degen et al. | 426/580 |
| 5,490,937 | 2/1996 | van Reis | 210/637 |
| 5,597,486 | * 1/1997 | Lutz | 210/639 |

FOREIGN PATENT DOCUMENTS

| | | |
|---|---|---|
| 0 249 932 A2 | 6/1987 | (EP) . |
| 0 467 482 | 1/1992 | (EP) . |
| 0 467 482 B1 | 4/1994 | (EP) . |
| 2 487 642 | 2/1982 | (FR) . |
| 2 179 947 | 7/1986 | (GB) . |
| WO 91/08216 | 6/1991 | (WO) . |
| WO 93/25567 | 12/1993 | (WO) . |
| WO 94/19935 | 9/1994 | (WO) . |
| WO 95/22258 | 8/1995 | (WO) . |

OTHER PUBLICATIONS

Harlow et al., Antibodies A Laboratory Manual Cold Spring Harbor Press p. 310, 1988.*

Bawden W. et al., *Biotechnology and Genetic Engineering Reviews*, 12:89–137, 1994.

(List continued on next page.)

*Primary Examiner*—Bennett Celsa
(74) *Attorney, Agent, or Firm*—Fish & Richardson P.C.

(57) ABSTRACT

A method of separating a soluble milk component from milk is disclosed. The method involves the use of tangential flow filtration across a membrane to form a retentate and a permeate, combining the permeate with the original milk sample, and repeating this procedure until the milk has been sufficiently purified. Preferably, the milk is combined with a chelating agent, such as EDTA, to improve the purification efficiency. This procedure is advantageously employed with milk from transgenic animals which have been genetically altered to express exogenous proteins, such as therapeutic proteins, in their milk.

16 Claims, 3 Drawing Sheets

OTHER PUBLICATIONS

Clark A.J. et al., *Biotechnology*, 7:487–492, 1989.
Clark A.J. et al., *Trends in Biotechnology*, 5:20–24, 1987.
Clark A. J. et al., *Journal of Cellular Biochemistry*, 49:121–127, 1992.
Dawson R., *Data for Biochemical Research*, 400–412, 1986.
Denman J. et al., *Biotechnology*, 9:839–843, 1991.
Rudolph N.S., *Genetic Engineering News*, 15:8–9, 1995.
Steimer K. S. et al., *Journal of Cell Biology*, 88:294–300, 1981.
Steimer K.S. et al., *Journal of Cell Biology*, 109:223–234, 1981.
Velander W, (1992) Purificatio Challenges for Recombinant Protein C From the Milk of Transgenic Pigs. Am. Chem.Soc. Abstr 203 Meeting Pt1:106(Abstract).*
Wilkins TD, et al, (1992) Isolation of recombinant proteins from milk. J Cell Biochem 49:333–338.*
Bawden, W et al., "The Genes Encoding the Major Milk-Specific Proteins and Their use in Transgenic Studies and Protein Engineering," *Biotechnology and Genetic Engineering Reviews* 12:89–137 (1994).
Clark, A.J., "Prospects for the Genetic Engineering of Milk," *Journal of Cellular Biochemistry*, 49:121–127 (1992).

Clark, A.J., "Expression of Human Anti–Hemophilic Factor IX in the Milk of Transgenic Sheep," *Biotechnology* 7:487–492 (1989).

Clark, A.J. et al., "Pharmaceuticals from Transgenic Livestock," *Trends in Biotechnology*, 5: 20–24 (1987).

Denman, J. et al., "Transgenic Expression of a Variant of Human Tissue–Type Plasminogen Activator in Goat Milk: Purification and Characterization of the Recombinant Enzyme," *Biotechnology* 9:839–843 (1991).

Rudolph, N.S., "Advances Continue in Production of Proteins in Transgenic Animal Milk," *Genetic Engineering News* 15:8–9 (1995).

Velander, W. et al., "Purification Challenges for Recombinant Protein C From the Milk of Transgenic Pigs," *Am. Chem. Soc. 203rd Meeting*, pt. 1, abst. 106 (1992).

Wilkins, T.D. and Velander, W., "Isolation of Recombinant Proteins From Milk" *Journal of Cellular Biochemistry* 49:333–338 (1992).

* cited by examiner

PURIFICATION OF BIOLOGICALLY ACTIVE PEPTIDES FROM MILK

BACKGROUND OF THE INVENTION

This invention relates generally to an improved method for purifying components of interest from milk. More specifically, it provides a method for obtaining peptides from raw whole milk, without prior processing to remove fats, lipids or particulate matter, by use of tangential flow filtration, preferably through a closed-loop continuous extraction system.

Milk from domestic animals has been used as a source of proteins and other products for the food and pharmaceutical industries for many years, and a variety of techniques are known for isolating these products. Milk is a colloidal suspension composed primarily of fats, lactose and proteins in water. Among ruminants and laboratory animals, milk contains an average of 30 to 140 grams of protein per liter, or about 4–17% by weight, depending on the species. The bulk of these proteins are caseins, which are complexed with calcium and phosphate in supramolecular structures known as micelles. The other major class of milk proteins is whey proteins, predominantly comprised of beta-lactoglobulin and alpha-lactalbumin, but also including lactoferrin, immunoglobulins, and serum albumin.

Milk proteins usually are isolated by a combination of processes. Raw milk first is fractionated to remove fats, for example, by skimming, centrifugation, sedimentation (H. E. Swaisgood, Developments in Dairy Chemistry, I: Chemistry of Milk Protein, Applied Science Publishers, NY, 1982), acid precipitation (U.S. Pat. No. 4,644,056) or enzymatic coagulation with rennin or chymotrypsin (Swaisgood, ibid.). Next, the major milk proteins may be fractionated into either a clear solution or a bulk precipitate from which the specific protein of interest may be readily purified.

Even recent improvements in milk protein isolation require a first process for removing fats and lipids, followed by filtration to recover components of the approximate size of the protein of interest. For example, French Patent No. 2487642 describes the isolation of milk proteins from skim milk or whey by membrane ultrafiltration in combination with exclusion chromatography or ion exchange chromatography. Whey is first produced by removing the casein by coagulation with rennet or lactic acid. U.S. Pat. No. 4,485,040 describes the isolation of an alpha-lactoglobulin-enriched product in the retentate from whey by two sequential ultrafiltration steps. U.S. Pat. No. 4,644,056 provides a method for purifying immunoglobulin from milk or colostrum by acid precipitation at pH 4.0–5.5, and sequential cross-flow filtration first on a membrane with 0.1–1.2 micrometer pore size to clarify the product pool and then on a membrane with a separation limit of 5–80 kd to concentrate it.

Similarly, U.S. Pat. No. 4,897,465 teaches the concentration and enrichment of a protein such as immunoglobulin from blood serum, egg yolks or whey by sequential ultrafiltration on metallic oxide membranes with a pH shift. Filtration is carried out first at a pH below the isoelectric point (pI) of the selected protein to remove bulk contaminants from the protein retentate, and next at a pH above the pI of the selected protein to retain impurities and pass the selected protein to the permeate. A different filtration concentration method is taught by European Patent No. EP 467 482 B1 in which defatted skim milk is reduced to pH 3–4, below the pI of the milk proteins, to solubilize both casein and whey proteins. Three successive rounds of ultrafiltration or diafiltration then concentrate the proteins to form a retentate containing 15–20% solids of which 90% is protein.

Alternatively, British Patent Application No. 2179947 discloses the isolation of lactoferrin from whey by ultrafiltration to concentrate the sample, followed by weak cation exchange chromatography at approximately a neutral pH. No measure of purity is reported. In PCT Publication No. WO 95/22258, a protein such as lactoferrin is recovered from milk that has been adjusted to high ionic strength by the addition of concentrated salt, followed by cation exchange chromatography.

In all of these methods, milk or a fraction thereof is first treated to remove fats, lipids, and other particulate matter that would foul filtration membranes or chromatography media. The initial fractions thus produced may consist of casein, whey, or total milk protein, from which the protein of interest is then isolated. However, these techniques present significant disadvantages, including the requirement for large and expensive batch and/or continuous centrifuges, low yields due to protein loss by entrapment during precipitation, and loss of biological activity of the protein of interest by precipitation methods requiring low pH. These limitations may be tolerated for relatively inexpensive proteins present in very large amounts and used as commodities in foodstuffs, e.g., in the production of cheese. However, they become a significant economic disincentive if the protein represents a small fraction of total milk protein, represents an expensive pharmaceutical, or consists of an enzyme or other therapeutically active protein that must retain its biological activity.

All of these conditions would obtain, for example, in the purification of a pharmaceutical protein from the milk of transgenic animals. Exogenous protein expression levels generally range from less than 1 to 10 or more grams per liter, depending on the protein and the species. In a product with a potential annual market value of, for example, $100 million, every 1% loss represents $1 million.

Methods are known in the art for expressing exogenous proteins at commercially feasible levels in the milk of transgenic animals. Commercial production of a wide range of proteins in the milk of transgenic livestock is now under development (A. J. Clark, et al., *Trends in Biotechnology*, 5:20–24, 1987; A. J. Clark, *Journal of Cellular Biochemistry* 49:121–127, 1992; W. Bawden et al., *Biotechnology and Genetic Engineering Reviews*, 12:89–137, 1994; N. S. Rudolph, *Genetic Engineering News*, 15:8–9, 1995). Exogenous peptides, and in particular human peptides, may be produced in milk at relatively high concentrations and in large volumes, providing continuous high-level output of normally processed peptides that are easily harvested from a renewable resource. Purification of these valuable proteins by conventional processes is subject to the yield and activity losses described above. For example, A. J. Clark et al. reported recovery of anti-hemophilic Factor IX of approximately 2.0–2.5% by acid precipitation of casein from milk obtained from transgenic ewes, for a loss of approximately 98% (A. J. Clark et al., *Biotechnology* 7:487–492, 1989). J. Denman et al. reported recovery of a long-acting variant of tissue plasminogen activator of about 25%, or a loss of 75%, by acid precipitation of milk caseins from transgenic goats (J. Denman et al., *Biotechnology* 9:839–843, 1991).

PCT Patent Publication No. WO 94/19935 discloses a method of isolating a biologically active protein from whole milk by stabilizing the solubility of total milk proteins with a positively charged agent such as arginine, imidazole or Bis-Tris. This treatment forms a clarified solution from which the protein may be isolated, e.g., by filtration through membranes that otherwise would become clogged by precipitated proteins. The concentration of the additive is high, on the order of 1–3 molar. In some cases, it may be preferable to minimize the large required amounts of particularly expensive agents, such as arginine, which in any case must be removed in subsequent purification steps. This method also requires a first centrifugation step to remove milk fat.

What is disclosed herein is an improvement over methods known in the art for isolating soluble milk components. The present invention reduces losses in yield by providing mild conditions that preserve biological activity in an efficient and cost-effective method suitable for large-scale production.

SUMMARY OF THE INVENTION

The present invention provides a method for isolating a soluble milk component, such as a peptide, in its biologically active form from whole milk or a milk fraction by tangential flow filtration. Unlike previous isolation methods, the method of this invention eliminates the need for a first fractionation of whole milk to remove fat and casein micelles, thereby simplifying the process and avoiding, costly losses of recovery and bioactivity. This method may be used in combination with additional purification steps to further remove contaminants and purify the component of interest.

In accordance with the invention, whole milk is subjected to tangential flow filtration, preferably across an ultrafiltration membrane of sufficient porosity to form a permeate (filtrate) comprising a soluble milk component and a retentate containing fat, other colloidal materials, particulates, viruses, mycoplasma, bacteria and somatic cells. The permeate is subjected to a capture procedure to substantially remove the soluble milk component, and the effluent from this capture procedure is combined with the original milk sample (retentate). This procedure is repeated until the soluble milk component is substantially recovered.

In an alternative embodiment of this invention, whole milk is subjected to tangential flow filtration, preferably across an ultrafiltration membrane to form a permeate comprising a soluble milk component and a retentate containing fat, other colloidal materials, particulates, viruses, mycoplasma, bacteria and somatic cells. The permeate is collected, and a sufficient volume of solution is added to the retentate to maintain constant volume as the permeate is removed. This procedure is repeated until the soluble milk component is substantially recovered.

Optionally, the permeate may be further treated by one or more capture procedures to remove any contaminants that may be present, thereby providing a purified preparation of the component of interest. These additional procedures may include ultrafiltration, affinity chromatography, ion exchange chromatography, hydrophobic interaction chromatography, reverse phase chromatography, or other types of capture chromatography which are well known to those skilled in the art.

Optionally, this procedure is operated as a closed-loop continuous extraction system, in which the permeate is conducted directly to the capture device, and the eluate from the capture procedure is conducted directly back to the retentate.

Optionally, the whole milk is first combined with a chelating agent such as ethylenediaminetetraacetic acid (EDTA) which, surprisingly, keeps the milk from clumping and improves the flow of permeate across the ultrafiltration filter. This combination of milk and chelating agent is subjected directly to tangential flow filtration as described above, without further processing.

Accordingly, it is an object of the present invention to provide an efficient method for isolating a soluble milk component from whole milk or a fraction thereof by tangential flow filtration across an ultrafiltration membrane.

It is a further object of the present invention to eliminate the need to first process the whole milk prior to filtration to remove fats, casein micelles, lipids and particulates which might otherwise foul the microporous filter.

It is a further object of the present invention to provide a method that specifically eliminates the need to first process the whole milk by steps such as precipitation or centrifugation, which entrap a portion of the soluble milk component and reduce its yield.

It is a further object of the present invention to provide a method that uses mild conditions, in particular avoiding organic solvents and extremes of pH and temperature, thereby preserving the biological activity of the soluble milk component.

It is a further object of the present invention to provide a closed-loop continuous extraction method that maintains a constant volume without dilution or volume expansion, making the method efficient and cost-effective for large-scale purification.

It is a further object of the present invention to provide a tangential flow filtration permeate that may be subjected to further purification steps to remove contaminants and thereby yield a purified soluble milk component, one or more of which steps may be included in the closed-loop continuous extraction system.

It is a further object of the present invention to provide a method that combines in a single sequential process tangential flow filtration and a capture procedure for separating a soluble milk component.

It is a further object of the present invention to provide a method of adding a chelating agent such as EDTA to improve permeate passage across the ultrafiltration membrane and to help reduce milk clumping and membrane fouling during the filtration process.

It is a further object of the present invention to provide a method in which the ultrafiltration and chromatography media are selected from media which may be cleaned and reused multiple times without substantial change in performance. Reuse of expensive media will substantially reduce the overall cost of purification.

DETAILED DESCRIPTION OF THE INVENTION

Figure 1:
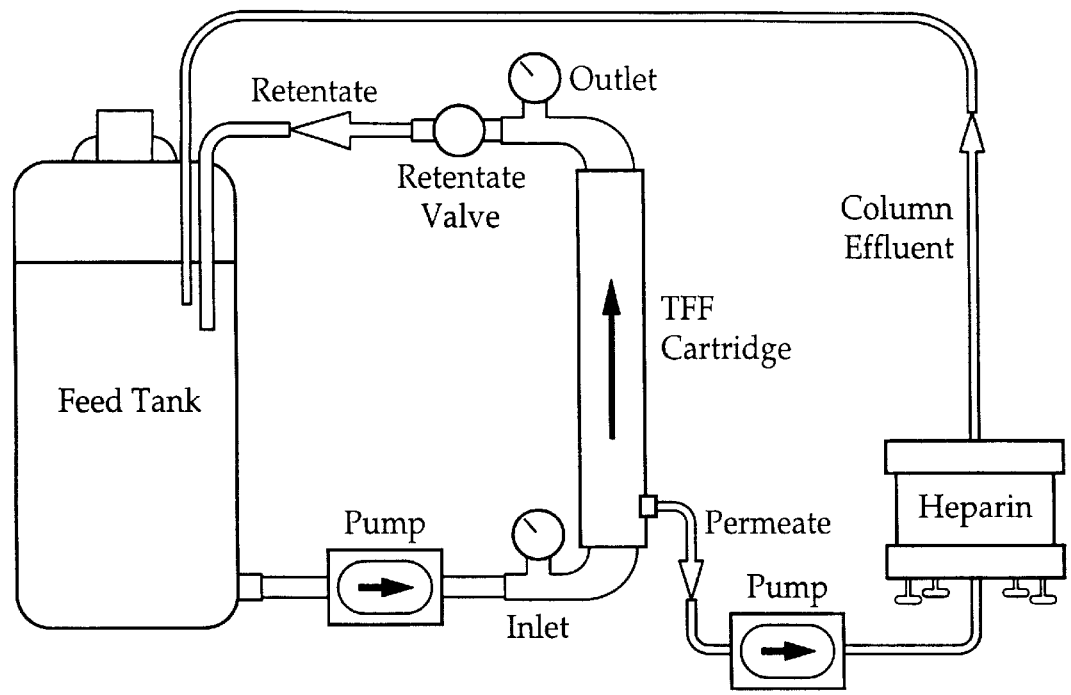
FIG. 1 is a schematic drawing of an exemplary apparatus used for the purification of biologically active peptides from milk in a closed loop continuous extraction system including tangential flow filtration and heparin affinity chromatography.

The present invention provides a method for isolating from milk a soluble milk component in its biologically active form. Preferably, the milk is whole milk. The soluble milk component may be either a component that is normally present in the milk of domestic animals, a component such as a specific antibody whose presence in milk is induced by immunization, a component whose presence in milk is induced or increased via specific foodstuffs, or an exogenous component that is introduced by gene transfer into a transgenic or transomic animal.

This soluble milk component may be a peptide and in particular, a protein. The protein may be, for example, a glycoprotein, immunoglobulin, enzyme, peptide or hormone. It may be a naturally occurring protein or a recombinant protein. It may be human or non-human in origin. It may be a potential therapeutic or pharmaceutical agent such as, but not limited to: alpha-1 proteinase inhibitor, alkaline phosphatase, angiogenin, antithrombin III, any of the blood clotting factors including Factor VIII, Factor IX, and Factor X, chitinase, extracellular superoxide dismutase, fibrinogen, glucocerebrosidase, glutamate decarboxylase, human serum albumin, immunoglobulin, insulin, myelin basic protein, proinsulin, soluble CD4 or a component or complex thereof, lactoferrin, lactoglobulin, lysozyme, lactalbumin, tissue plasminogen activator or a variant thereof.

Alternatively, the milk component may be used as an ingredient for foodstuffs, for example, to increase the nutritional value of bread (U.S. Pat. No. 5,178,894) or infant formula (PCT Publication No. WO 91/08216), or to add body, texture or stability to dairy products such as frozen dairy desserts (U.S. Pat. No. 5,175,013). It also may used as an additive for serum-free culture of certain types of cells, such as epithelial cells or fibroblasts (K. S. Steimer, et al., *J. Cell Physiol.* 109:223–234, 1981; K. S. Steimer and M. Klagsbrun, *J. Cell Biol.* 88:294–300, 1981). Additionally, it may be an industrial enzyme such as protease, lipase or chitinase (PCT Publication No. WO 93/25567).

The milk may be collected from a lactating mammal such as cow, goat, pig, rabbit, mouse, rat or sheep. The mammal may be either an ordinary laboratory or domestic animal, or a transgenic or transomic animal. As used herein, transgenic or transomic animal shall refer to a non-human animal. A transgenic animal is generally defined as an animal that expresses a peptide or other trait from a different species as a result of stable incorporation of one or more foreign genes into its genome. Such a peptide is referred to as an exogenous peptide. Secretion of exogenous peptides in the milk of transgenic mammals is accomplished by using methods known in the art for introducing into a fertilized egg or embryo a fusion or recombinant gene construct that includes protein coding sequences plus regulatory sequences from a milk-specific protein such as casein, whey acidic protein or lactoglobulin. These fusion constructs may direct the expression of an exogenous protein predominantly or exclusively to milk, in concentrations high enough to render its isolation commercially feasible.

The milk also may be collected from a transomic animal, also called a transomatic animal, which is an animal that expresses a protein or trait from another species as a result of introduction of one or more foreign genes into a particular somatic tissue. For example, exogenous proteins may be produced in milk by the introduction of appropriate genes and regulatory elements directly into mammary epithelial cells, for example, by retroviral vectors that target the rapidly dividing myoepithelial cells in the mammary gland. Unlike transgenic animals, which transmit the transgene to their progeny through successive generations, transomic animals do not transmit the ability to produce exogenous proteins in their milk but must be created individually. Nonetheless, they may be sources of proteins or other components of interest.

An exogenous peptide that normally is not produced by the mammal is known as a heterologous peptide. Examples of heterologous peptides that may be found in the milk of domestic animals include human milk proteins such as lactoferrin, human serum proteins such as blood clotting factors, and industrial enzymes such as chitinase. A peptide that normally is produced by the particular mammal is known as an endogenous peptide. Examples of endogenous peptides include milk proteins and serum proteins specific to the particular mammal. A mammal may be made transgenic to express an endogenous milk protein with the purpose of increasing its concentration, or to express in milk a protein normally found only in the serum. For example, bovine transferrin normally is present in trace amounts in milk, but expression may be increased significantly by generating a transgenic animal bearing the lactoferrin gene under the control of an alpha-S1 casein gene (PCT Publication No. WO 93/25567).

A heterologous peptide may co-exist with an endogenous form of the same peptide or protein that normally is produced by the transgenic mammal. Heterologous and homologous forms of a peptide usually differ by one or more of amino acid sequence, tertiary or quaternary structure, glycosylation or other post-translational modification. For example, antithrombin III in transgenic sheep exists in both human and ovine forms which may be distinguished by amino acid sequence differences that may result in differences in protein surface charge, hydrophobicity, metal binding affinity or other affinities. For uses such as human pharmaceuticals or therapeutics, human peptides are preferred because they are less likely to be recognized as foreign proteins by the intended human recipients. If non-human forms of the peptide are present in the milk of the mammal, it may be necessary to separate them from the exogenous human protein as a part of the purification process.

The present invention encompasses any component of interest that may be present in milk, whether naturally occurring or induced, whether endogenous or exogenous, and whether homologous or heterogolous.

Milk may be processed by the method of the present invention in the form of either raw, pasteurized or frozen whole milk. This eliminates the need for a first step to remove fats, casein micelles, lipids, somatic cells, and other particulate matter that may be present in the milk and that may foul microporous filtration membranes or chromatography media. Typically, this first step is carried out either by precipitation of protein fractions with acid or rennet, or by centrifugation and skimming off of the fats and lipids to produce skim milk. All of these methods are known to entrap proteins and reduce their recovery. Furthermore, precipitation methods require additional steps to resolubilize and clarify the precipitated proteins for further processing. Because bulk centrifugation requires large and expensive equipment, this processing step may be scaled up only by replacing existing centrifuges with larger ones, adding more centrifuges and running several of them in parallel, or sequentially processing multiple batches through the existing centrifuge(s), thereby prolonging the total processing time.

In addition, the low pH required for protein precipitation may reduce or destroy the biological activity of some components of interest. For example, the thrombin inhibitor antithrombin III is unstable at pH values less than approximately 6.0 and is completely inactivated at pH values of 3–5, which typically are used for acid precipitation of casein proteins.

In the present invention, losses due to entrapment and acid lability are eliminated by a method in which prior fractionation of whole milk is not required. According to this method, milk is subjected directly to filtration across a microporous membrane. Examples of filtration include dead-end filtration and tangential flow filtration. In dead-end filtration, the solution to be filtered flows perpendicular to the filter surface. In tangential flow filtration, the solution to be filtered flows parallel to the filter and the permeate diffuses across it. In the method of this invention, the filtration is by tangential flow filtration.

The filter used for tangential flow filtration preferably has a porosity sufficient to form a permeate containing the milk component of interest and a retentate containing the fats, cells, casein micelles, and particulates. In general, milk fat globules may be retained by membranes with a pore size of approximately <1–10 micrometers, somatic cells with a pore size of approximately 0.450 micrometer, bacteria with a pore size of approximately 0.200 micrometer, casein micelles with a pore size of approximately 0.08–0.20 micrometer, viruses with a pore size of approximately 0.05–0.1 micrometer, mycoplasma with a pore size of 0.1 micrometer, and prions with a pore size of approximately 0.35 micrometer. A membrane sufficient to remove viruses is presumed also to remove fat globules, somatic cells, bacteria, and casein micelles. A pore size of approximately 0.05 micrometer generally corresponds to a molecular weight cut-off of approximately 500 kD.

Ordinarily, in tangential flow filtration across an ultrafiltration membrane, the component of interest is concentrated in the retentate. For example, EPO Publication No. 467,482 discloses the purification of combined milk proteins by ultrafiltration of acidified skim milk, followed by diafiltration and a second ultrafiltration, in each case retaining the proteins in the retentate. What is novel about the present invention, however, is the use of an ultrafiltration membrane to separate the soluble milk components into the permeate. The permeate thus formed is a clear solution which is suitable for optional further processing to isolate and purify and component of interest. The retentate remains milky in appearance.

Optionally, milk is first combined with a chelating agent under mild conditions in an amount sufficient to prevent the raw milk from clumping and fouling the filtration membranes and to improve passage of permeate across the membrane. As used herein, a chelating agent is defined as any agent capable of solubilizing organic or inorganic calcium salts. Preferably, the chelating agent is capable of chelating calcium. Examples of chelating agents that effectively chelate calcium are ethylenediaminetetraacetic acid (EDTA), ethylene glycol-bis (beta-aminoethyl ether) N,N,N',N' tetraacetic acid (EGTA) or citrate. Preferably, the chelating agent is added to produce a final concentration of between 1 and 500 mM. Most preferably, the final concentration of chelating agent is approximately 20 to 50 mM EDTA or 50 to 200 mM citrate.

In some circumstances, citrate may be preferred over the stronger chelator EDTA because disposal of EDTA may subject to environmental regulation, depending on the total amount to be discarded, and therefore may be more costly. EGTA has a higher affinity constant for calcium than does EDTA (R. M. C. Dawson, D. C. Elliott, W. H. Elliott, and K. M. Jones, Data for Biochemical Research, 3rd Ed., Clarendon Press, Oxford, 1986) and should be equally or more effective in the method of this invention.

A further advantage of the present invention is that membranes that do not become fouled by clogging are more easily cleaned and reused. For example, they may be cleaned in place by repeated washing in situ with appropriate solvents such as acids, bases and/or alcohols. Prior to reuse, these membranes are equilibrated with appropriate buffers to remove all traces of the solvents. By providing methods amenable to the recycling of filtration membranes, which may cost tens of thousands of dollars in the amounts required for large-scale purification, this invention substantially reduces processing costs.

In the preferred embodiment of this invention, tangential flow filtration across an ultrafiltration membrane is combined in a single sequential process with a capture step to remove the soluble milk component from the permeate. Most preferably, tangential flow filtration is carried out with a closed-loop continuous extraction system. The permeate is conducted directly to a capture device to isolate the soluble milk component. A schematic drawing of an exemplary apparatus used to practice this method is shown in FIG. 1.

Under conditions that maintain constant volume and constant product passage, this recovery process may be modeled by an exponential decay equation, hereinafter referred to as Equation 1:

$$Cr = Co \times e^{-(Vp \times d/Vo)}$$

where:
Cr is the concentration of the desired component in the retentate
Co is the starting concentration of the desired component
Vo is the starting volume
Vp is the total permeate volume
d=is the passage coefficient (or the ratio of Cr/Co at any given time)

For example, the method of this invention may be used to isolate antithrombin III from whole milk from a transgenic goat. In this case, the milk would be processed by tangential flow filtration across a 500 kD filter followed by a capture step onto a heparin affinity chromatography column. Under conditions that maintain constant flux, approximately 40% of the antithrombin III in the retentate passes through the membrane at any given time: that is, the passage coefficient, denoted as d in Equation 1, equals 0.4. Equation 1 predicts that after 7 volumes of diluted milk is passed to the permeate and onto the heparin affinity column, 94% of the antithrombin III in the original milk sample may be recovered. In practice, recovery rates after 7 sample passes are 75–90%.

Most preferably, the effluent from this capture device is conducted in-line back to the original milk sample reservoir containing the retentate. Substantially all of the component of interest is captured, and the liquid from the fluid stream is returned to the original milk sample reservoir. Residual amounts of the component of interest that remain in the retentate may be isolated by continuing the filtration/chromatography process.

Figure 2:
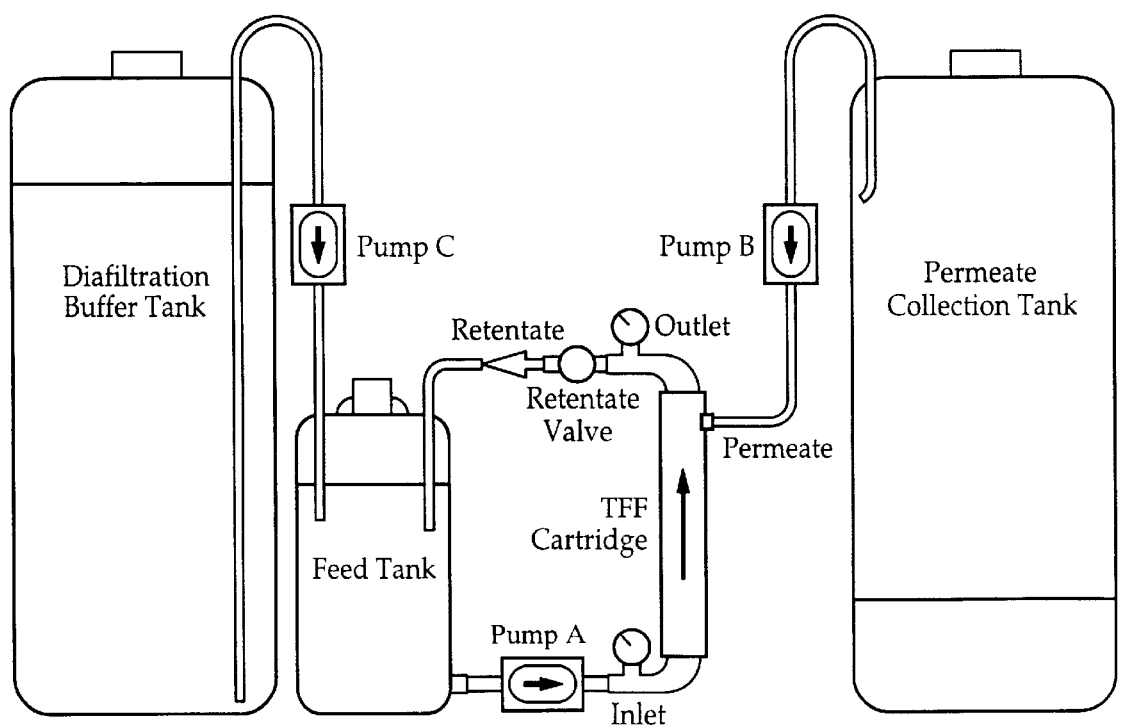
FIG. 2 is a schematic drawing of an exemplary apparatus used for the isolation of biologically active peptides from milk by tangential flow filtration.

In an alternative embodiment, the permeate is removed to a reservoir and replaced with a sufficient volume of buffer solution to maintain constant volume in the milk sample reservoir. A schematic drawing of an exemplary apparatus used to practice this alternative method is shown in FIG. 2.

Ordinarily, continuous flow filtration processes such as ultrafiltration and diafiltration are carried out by simultaneously adding water or buffer at the same rate at which permeate is eliminated. This results in a significant increase in the total volume of sample and waste solutions and in the size of the containers needed to process and hold them. However, the method of this invention maintains constant volume. Preferably the milk solution is maintained as concentrated as is feasible to allow efficient filtration without clogging the membrane. In addition, the various milk components remain in equilibrium, except for the selective removal of the component of interest. Advantageously, the process described herein minimizes the total volume of starting sample, retentate and permeate, the required volume of buffer, the size of the collection containers and buffer reservoirs, the total size of the physical plant and the number of individuals required to staff the purification facility. This invention thus represents a considerable potential cost savings over conventional purification methods. The permeate produced by tangential flow filtration according to the method of this invention comprises a partially purified preparation of the component of interest.

In a further application of the present invention, this permeate optionally may be treated by one or more additional processes to remove the chelating agent along with other contaminants that may be present to provide a purified preparation of the component of interest. The first permeate may contain additional peptides of molecular weight similar to, larger or smaller than the component of interest. These may be, for example, other endogenous milk proteins or homologous forms of the exogenous protein. Examples of additional processes suitable for further purification include affinity chromatography, ion exchange chromatography, hydrophobic interaction chromatography, thiophilic chromatography, metal chelate chromatography, reverse phase chromatography or filtration processes such as ultrafiltration. Affinity chromatography may be carried out with ligands that specifically or preferentially bind the component of interest, such as an antibody, Protein A or Protein G or, in the case of antithrombin III, heparin.

EXAMPLE 1

Isolation of a Biologically Active Antithrombin III from Milk

Milk was collected from transgenic goats expressing antithrombin III and frozen at −35 degrees C. The frozen milk was thawed either overnight in a cold room at 8+3 degrees C., or in a water bath at ≦40 degrees C. with intermittent manual swirling until thawing was complete. A sample of approximately 23 kg of thawed milk was combined with an equal weight of a solution containing 50 mM EDTA and 180 mM sodium chloride, pH 9.1, at 8+3 degrees C.

The diluted milk was placed in a feed tank and clarified at 8+6 degrees C. by tangential flow filtration in a continuous extraction system illustrated schematically in FIG. 1. Hollow fiber membrane cartridges with a 500 (kD) molecular weight cut-off (UFP-500-E; A/G Technology Corp., Needham Mass.) were equilibrated with a solution containing 10 mM EDTA and 180 mM sodium chloride at pH 6.8. The milk was circulated through six 0.7 m² cartridges arranged in three parallel stacks of two at a flow rate of ≦45 L/min established by means of a centrifugal pump. The inlet pressure was adjusted to 15+2 pounds per square inch (psi) by a diaphragm valve. The permeate flow rate was regulated by means of a metering pump to maintain permeate transmembrane pressure at 0 to 5 psi. A heat exchanger (not shown in FIG. 1) was included in the line just before the filtration cartridges to maintain solution temperature near 8 degrees C.

The permeate containing antithrombin III was pumped directly in-line to an equilibrated affinity chromatography column containing derivatized heparin as the ligand. The Heparin HyperD resin (BioSepra Inc., Marlborough Mass.) was packed into a chromatographic column to create a total bed volume of 6.1±0.7 L and equilibrated with 10 mM EDTA in 180 mM sodium chloride, pH 6.8 at 8±3 degrees C. Effluent from the heparin column was passed directly back into the feed tank. The milk sample, now combined with filtration retentate and heparin column effluent, was recirculated until a total of 7 volumes of diluted milk were passed through the filtration cartridges. The heparin column then was disconnected from the tangential flow filtration unit and was washed with buffer containing 20 mM sodium phosphate and 400 mM sodium chloride, pH 7.0. Antithrombin III was eluted with buffer containing 20 mM sodium phosphate and 2.5 M sodium chloride, pH 7.0. Protein in the column effluent was detected with a UV absorbance detector fitted with a 280 nanometer filter.

The entire process of tangential flow filtration and heparin chromatography took approximately 6–8 hr. We had previously demonstrated that under the conditions described herein, the flux across this type of 500 kD ultrafiltration hollow fiber cartridge remained constant for 4 hr. Prior experiments also established that other types of membranes, such as 0.1 micrometer, 0.2 micrometer and 0.45 micrometer Durapore membranes, were less suitable for tangential flow filtration under the conditions stipulated herein because the flux decreased significantly over a 30-min trial filtration period.

Quantitative reverse-phase chromatography was used to measure total antithrombin III protein in the starting milk sample and final heparin column eluate. A POROS R2/H column (Product No. 1-1114-12, PerSeptive BioSystems, Cambridge, Mass.) was used according to manufacturer's instructions. A column gradient of 0.1% trifluoroacetic acid (TFA) in water to 0.1% TFA in 99.9% acetonitrile was established at a flow rate of 2.0 mL per minute, and was calibrated with a standard solution of antithrombin III. Antithrombin III content was interpolated from a linear standard curve.

Antithrombin III biological activity was determined by a thrombin inhibition assay that measured the extent to which antithrombin III in the samples inhibited the cleavage of Kabi substrate S2238 (H-D-Phenylalanyl-L-pipecolyl-L-arginine-p-nitroaniline dihydrochloride) by a standard amount of thrombin. Heparin, which binds both thrombin and antithrombin III, was added to each assay sample to enhance antithrombin III inhibiting activity. Heparin and thrombin were incubated in microwell plates with aliquots of either process samples or dilutions of a standard antithrombin III solution. After incubation for 15 min at 37 degrees C., the reaction was stopped with glacial acetic acid, and absorbance was measured at 405 nanometers. Antithrombin III activity was interpolated from a linear standard curve.

This combination of tangential flow filtration and heparin affinity chromatography consistently yielded a recovery of 75% to 90%, with purity exceeding 95%. Results for a typical purification run for lot AT501 are shown in Table 1. The starting milk sample of 24 L contained a total of 55 g antithrombin III, of which 42 g (75%) was recovered from the heparin affinity column. The final product pool had a specific activity of 7.8 Units/mg, which is comparable to that of plasma-derived antithrombin III.

Had tangential flow filtration been conducted alone and not combined in-line with heparin affinity chromatography, then permeate would have been removed to a collection tank and a volume of buffer equal to the volume of permeate removed would have been added to the milk/retentate reservoir to maintain constant volume. An exemplary apparatus is illustrated in FIG. 2. For a typical purification run for lot AT501, for example, a total permeate of 331 L would have been collected, and an equal volume of buffer would have been added back into the system.

EXAMPLE 2
Effect of EDTA on the Filterability of Whole Milk

Twenty mL aliquots of whole goat milk, frozen and thawed as described in Example 1, were combined with 20 mL of 50 mM EDTA or 20 mL of distilled deionized water, and adjusted to different pHs over the range 6 to 10 with concentrated HCl or NaOH. Each solution was diluted twice more with distilled deionized water to final milk dilutions of 1/16 and 1/32 (vol/vol). Individual samples were pumped through sterile 0.22 micrometer Millex-GV filters (Millipore Corp., Bedford, Mass.) at flow rates of 3 mL/min until to a pressure of 20 PSIG was reached. The permeates were collected into small pre-weighed tubes. Each filtration was carried out in duplicate. Tubes were weighed to calculate the total permeate in grams, and this was converted to volume. Controls were treated in exactly the same way except that they received no EDTA. In some cases, permeates were assayed for antithrombin III activity by the thrombin inhibition assay as described in Example 1.

Figure 3A:
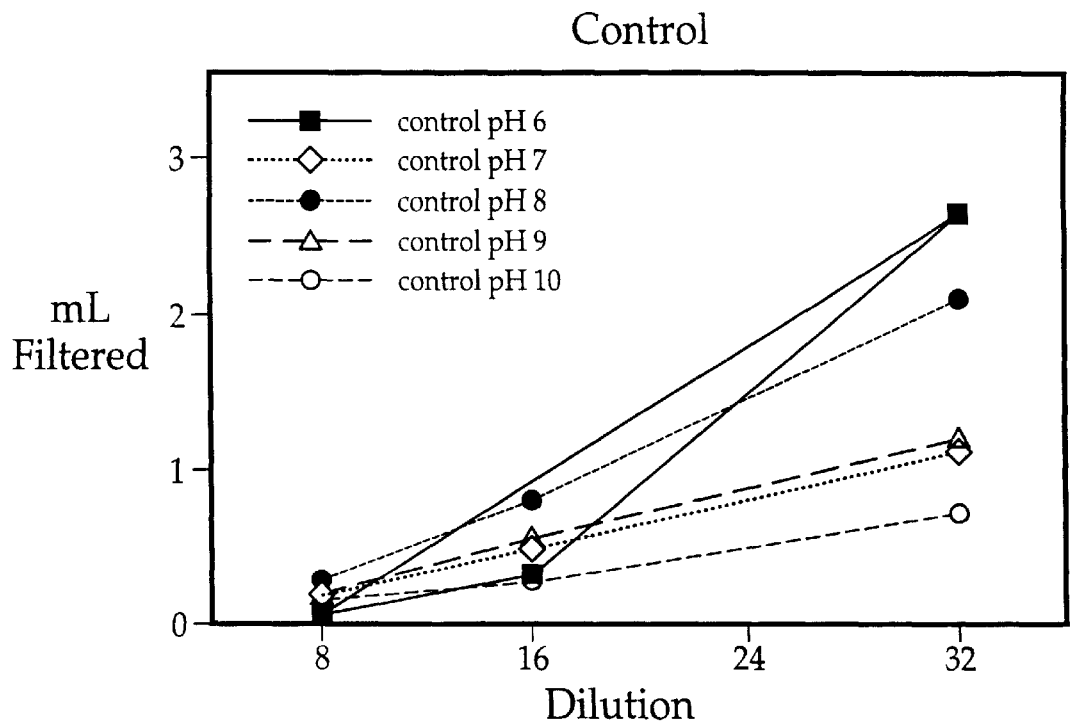
FIGS. 3A and 3B depict the effect of EDTA at different pH values on the filterability of whole milk.
Figure 3B:
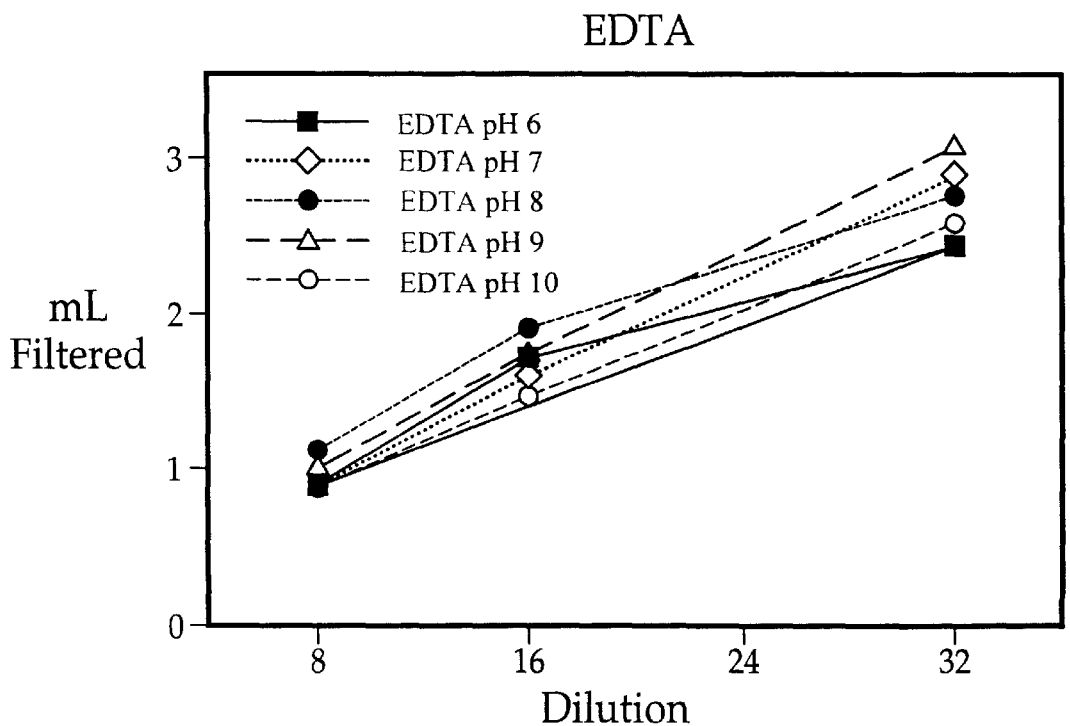

Milk diluted in water alone at pH $\leq 8$ passed readily through the filters at a final dilution of 1/32 (FIG. 3). However, the addition of EDTA increased filterability at all pHs and at all concentrations tested. EDTA was particularly effective at the lower dilutions tested, which would correspond to smaller total processing volume in full-scale purification operations. In a separate experiment, a two-fold increase in EDTA concentration at pH 8 yielded at least a two-fold increase in total weight of milk filtered over the range 6.25 to 25 mM EDTA (data not shown).

EXAMPLE 3
Effect of Different Chelating Agents on the Isolation of a Soluble Protein from Milk Milk from transgenic goat 155-10, which expressed antithrombin III, was collected, frozen and thawed as described in Example 1. Samples of 160 mL of thawed milk were combined with an equal weight of buffer containing either EDTA or citrate as the chelating agent.

The citrate buffer contained 166 mM sodium citrate and 10 mM citric acid, pH 7.0. The diluted milk was clarified at 8±6 degrees C. by tangential flow filtration in a continuous extraction system as described in FIG. 1, but on a smaller scale. A hollow fiber membrane cartridge with a 500 kD molecular weight cut-off (UFP-500-E-4; A/G Technology Corp., Needham Mass.) was equilibrated with a solution containing 118 mM sodium citrate and 7 mM citric acid, pH 7.0. The milk was recirculated through a 0.032 m² cartridge at 2.5 L/min by means of a peristaltic pump. The inlet pressure was adjusted to 15±2 psi with a tubing clamp. A second peristaltic pump was used to maintain flow rate at 18 mL/min and pressure at 2 to 6 psi.

The permeate containing antithrombin III was pumped directly in-line to an equilibrated Heparin HyperD (BioSepra Inc., Marlborough Mass.) affinity column. The column was 76 mL and was equilibrated with 118 mM sodium citrate and 7 mM citric acid, pH 7.0 at 8±6 degrees C. The permeate was passed directly onto the heparin column and the heparin column effluent was passed back to the retentate reservoir in a closed-loop continuous extraction system.

After 13 volumes of diluted milk were passed through the filtration cartridges, the heparin column was disconnected from the tangential flow filtration unit. The heparin column was washed with a buffer containing 20 mM sodium phosphate and 400 mM sodium chloride, pH 7.0. Antithrombin III was eluted from the heparin column with a buffer containing 20 mM sodium phosphate and 2.5 M sodium chloride, pH 7.0. Protein in the column elution was detected with a UV absorbance detector fitted with a 280 nanometer filter. The entire process of tangential flow filtration and heparin chromatography took approximately 6 hr.

Whole milk combined with EDTA as the chelating agent was processed similarly at this scale using the buffers and column wash solutions described in Example 1.

Figure 4:
FIG. 4 depicts an electrophorogram of a silver stained SDS-polyacrylamide gel demonstrating the effect of different chelating agents on the purity of antithrombin isolated from milk.

Aliquots of purified antithrombin III were separated by electrophoresis on an SDS-polyacrylamide gel with a 10–20% gradient (Owl Scientific Woburn, Mass.) and stained with silver according to standard methods for qualitative assessment of protein purity. FIG. 4 shows heparin column effluents from the EDTA and citrate samples (Lanes 3 and 5, respectively), and eluted protein from the LDTA and citrate processes (Lanes 7 and 9, respectively). Molecular weight standards were from BioRad Hercules, Calif. (product no. 161-0304). Similar purity levels were obtained from both the EDTA and citrate processes. As determined by quantitative reverse-phase chromatography, recovery of antithrombin III activity was 81% with EDTA and 90% with citrate.

EXAMPLE 4
Isolation of a Biologically Active Monoclonal Antibody from Milk

Milk collected from transgenic goat 395-94, which expressed an IgG monoclonal antibody, was frozen, thawed, combined with EDTA and processed essentially as described in Example 1. The sample was subjected to tangential flow filtration through either a 500 kilodalton (kD) molecular weight cut-off hollow fiber filter (Model UFP-500-E-3A, A/G Technology Corp., Needham, Mass.) or a 0.1 micron hollow fiber filter (Model CFP-1-E-3A, A/G Technology Corp., Needham, Mass.). In both cases the permeate was conducted directly onto a Protein G affinity chromatography column (Pharmacia, Piscataway, N.J.). The columns were equilibrated with 0.1 M sodium phosphate, pH 7.0 and after the tangential flow filtration step had been completed, washed with 0.1 M sodium phosphate, pH 7.0 and eluted with 0.1 M citric acid, pH 2.2. The purity of the IgG in the original milk sample was approximately 21% as determined by quantitative reverse phase chromatography. After tangential flow filtration and Protein G chromatography, the IgG purity was at 82% for the 0.1 micron filtered material and 99% for the 500 kD filtered material.

EXAMPLE 5
Removal of Viruses from a Biological Preparation

Virus removal studies were performed on the process of this invention by a contract research organization according to standard testing procedures. The isolation of antithrombin III from whole milk was carried out as described in Example 1, except that the process was scaled down by using narrower diameter columns with the same bed heights used in process-scale manufacturing. Other key parameters remained unchanged, such as the ratio of antithrombin III protein to column bed volume in the heparin affinity column, linear flow rates, ratios of buffer volume to column volume, buffer composition and temperature.

Four viruses were selected as representative of the range of pathogenic virus types to which goats in North America might be susceptible. Two enveloped viruses were tested: xenotropic murine retrovirus, a single-stranded (ss) RNA-containing virus of the family Retroviridae, which was tested on Mink S+L-target cells; and pseudorabies virus, a double-stranded (ds) DNA virus of the family Herpesviridae, which was tested on PK-13 cells (ATCC CRL 6489). Two non-enveloped viruses were tested: Poliovirus Sabin Type 1, a ss RNA virus of the family Picornaviridae, tested on Vero cells (ATCC CCL 81); and mouse adenovirus, a ds DNA virus of the family Adenoviridae, tesed on BALB/c 3T3 cells.

The milk samples were spiked separately with known innocula of each virus and processed by tangential flow filtration and heparin affinity column chromatography. The loading solution for the heparin column also was spiked separately. Effluents from both columns were tested individually on cultures of each target cell type. The tangential flow filtration column consistently gave good viral reduction with all four viruses, and the larger Pseudorabies virus and Xenotropic murine retrovirus were completely removed. The heparin affinity column gave 2–4 log viral reduction. Results are summarized in Table 2.

TABLE 1

Isolation of antithrombin III from the milk of transgenic goats by the method of this invention, using tangential flow filtration combined with heparin affinity chromatography. Results are shown for a typical purification for lot AT501, as described in Example 1. Antithrombin III (ATIII) activity was measured by thrombin inhibition assay and expressed in killiunits (KU); total ATIII protein was measured by quantitative reverse-phase chromatography.

| Step | Volume, L | ATIII activity, KU/L | Total ATIII, KU | ATIII Protein, g/L | Total ATIII, g | % Yield |
|---|---|---|---|---|---|---|
| Milk | 23.9 | 19.2 | 457 | 2.32 | 55.3 | 100 |
| Diluted Milk | 47.0 | 10.3 | 485 | 1.13 | 53.2 | 96 |
| Permeate | 331 | | | | | |
| Heparin Eluate | 8.0 | 49.1 | 390 | 5.24 | 41.7 | 75 |

TABLE 2

Virus reduction by the antithrombin III isolation process, measured by spiking each column separately with virus innocula and culturing column effluents on appropriate target cultured cells.

| | Log(10) Reduction | | |
|---|---|---|---|
| Virus | Tangential flow filtration column | Heparin affinity column | Total |
| Enveloped viruses | | | |
| Xenotropic murine retrovirus | >4.3 | 2.9 | >7.2 |
| Pseudorabies virus | >4.2 | 1.2 | >5.4 |
| Non-enveloped viruses | | | |
| Poliovirus Sabin Type 1 | 4.1 | 4.0 | 8.1 |
| Mouse adenovirus | 3.5 | 2.3 | 5.8 |

What is claimed is:

1. A method of separating an exogenous component from a milk sample, comprising:

a) subjecting the milk sample containing at least one of the following: fat, casein micelles, somatic cells or particulate matter, to tangential flow filtration across a membrane of sufficient porosity to form a retentate and a permeate comprising the exogenous component;

b) subjecting the permeate to a chromatography capture device to remove the exogenous component and providing an effluent;

c) combining the effluent with the retentate; and d) repeating Steps a) through c) at least once and until the exogenous component is free of fat, casein micelles, somatic cells or particulate matter, and wherein the recovery of the exogenous component is 75–90%.

2. The method of claim 1 wherein the milk or milk fraction is combined with a chelating agent in an amount sufficient to reduce milk clumping and to improve passage through the filtration membrane.

3. The method of claim 1 wherein the component is a peptide or protein.

4. The method of claim 3 wherein the protein is selected from the group consisting of glycoproteins, immunoglobulins, peptides, hormones, enzymes, serum proteins, milk proteins, cellular proteins, soluble receptors and industrial enzymes.

5. The method of claim 4 wherein the protein is selected from the group consisting of alpha-1 proteinase inhibitor, alkaline phosphatase, angiogenin, antithrombin III, chitinase, extracellular superoxide dismutase, Factor VIII, Factor IX, Factor X, fibrinogen, glucocerebrosidase, glutamate decarboxylase, human serum albumin, insulin, myelin basic protein, lactoferrin, lactoglobulin, lysozyme, lactalbumin, proinsulin, soluble CD4, component and complexes of soluble CD4, tissue plasminogen activator and a variant thereof.

6. The method of claim 1 wherein tangential flow filter has a pore size in the range from 0.1 to 1,000 nanometers.

7. The method of claim 1 wherein bacteria, mycoplasma, viruses, prion particles and other microbial contaminants present in the raw milk are removed.

8. The method of claim 2 wherein the chelating agent is selected from the group consisting of EDTA, EGTA and citrate.

9. The method of claim 8 wherein the chelating agent is added to a final concentration range from 1 to 500 millimolar.

10. The method of claim 1 wherein the milk is obtained from a lactating non-human mammal selected from the group comprising transgenic mammals and transomic mammals.

11. The method of claim 10 wherein the milk is obtained from a transgenic cow, goat, pig, rabbit, mouse, rat or sheep.

12. The method of claim 8 wherein the chelating agent is EDTA.

13. The method of claim 12 wherein the EDTA is added to a final concentration of about 20 to 50 millimolar.

14. The method of claim 1 wherein the chromatography capture device is an affinity chromatograhy capture device.

15. The method of claim 14 wherein the affinity chromatography capture device is selected from the group consisting of heparin column, Protein A column or Protein G column.

16. The method of claim 14 wherein the chromatography capture device is an ion exchange chromatography capture device.

* * * * *